(12) United States Patent
Tischler et al.

(10) Patent No.: US 8,348,993 B2
(45) Date of Patent: Jan. 8, 2013

(54) FLEXIBLE STENT DESIGN

(75) Inventors: Brian Tischler, New Brighton, MN (US); Ben Bidne, Buffalo, MN (US); Dennis Peiffer, Brooklyn Park, MN (US); James F. Hemerick, Brooklyn Park, MN (US); Chad Perrin, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 41 days.

(21) Appl. No.: 13/036,480

(22) Filed: Feb. 28, 2011

(65) Prior Publication Data
US 2011/0238156 A1 Sep. 29, 2011

Related U.S. Application Data

(60) Provisional application No. 61/318,554, filed on Mar. 29, 2010.

(51) Int. Cl.
A61F 2/82 (2006.01)
(52) U.S. Cl. .................................................. 623/1.16
(58) Field of Classification Search ......... 623/1.11–1.34
See application file for complete search history.

(56) References Cited

U.S. PATENT DOCUMENTS

| | | | |
|---|---|---|---|
| 5,938,697 A | 8/1999 | Killion et al. | |
| 6,334,871 B1 | 1/2002 | Dor et al. | |
| 6,709,453 B2 * | 3/2004 | Pinchasik et al. | 623/1.15 |
| 6,776,793 B2 | 8/2004 | Brown et al. | |
| 6,863,685 B2 | 3/2005 | Davila et al. | |
| 7,112,216 B2 | 9/2006 | Gregorich | |
| 7,223,283 B2 | 5/2007 | Chouinard | |
| 7,316,710 B1 | 1/2008 | Cheng et al. | |
| 7,381,217 B2 | 6/2008 | Tischler | |
| 2003/0074056 A1 | 4/2003 | Killion et al. | |
| 2004/0073291 A1 * | 4/2004 | Brown et al. | 623/1.15 |
| 2005/0107865 A1 | 5/2005 | Clifford et al. | |
| 2005/0182480 A1 * | 8/2005 | Doran et al. | 623/1.15 |
| 2007/0073384 A1 | 3/2007 | Brown et al. | |
| 2008/0065194 A1 * | 3/2008 | Dakin et al. | 623/1.16 |
| 2008/0065195 A1 | 3/2008 | Brown et al. | |
| 2009/0105797 A1 * | 4/2009 | Roeder et al. | 623/1.2 |
| 2010/0010622 A1 | 1/2010 | Lowe et al. | |
| 2011/0004292 A1 * | 1/2011 | Davis et al. | 623/1.16 |

FOREIGN PATENT DOCUMENTS

| | | |
|---|---|---|
| WO | 9938457 | 8/1999 |
| WO | 2006127784 | 11/2006 |

OTHER PUBLICATIONS

Notification of Transmittal of the International Search Report and the Written Opinion of the ISA, PCT/US2011/026464, mailed Jul. 5, 2011.

* cited by examiner

*Primary Examiner* — Suzette J Gherbi
(74) *Attorney, Agent, or Firm* — Vidas, Arrett & Steinkraus, P.A.

(57) ABSTRACT

Stents having a plurality of serpentine bands including a proximal end portion, a distal end portion, and a middle portion therebetween are herein disclosed. Each of the bands includes peaks and valleys. Serpentine bands of the proximal end portion are connected together in a repeating pattern of connected and unconnected peaks and valleys. Serpentine bands of the distal end portion are connected together in a repeating pattern of connected and unconnected peaks and valleys. The repeating pattern of the proximal end portion is different than the repeating pattern of the distal end portion.

15 Claims, 7 Drawing Sheets

FLEXIBLE STENT DESIGN

CROSS-REFERENCE TO RELATED APPLICATIONS

This Application is a non-provisional of Application No. 61/318,554, filed Mar. 29, 2010, which is herein incorporated by reference.

STATEMENT REGARDING FEDERALLY SPONSORED RESEARCH

Not Applicable

BACKGROUND OF THE INVENTION

A stent is a medical device introduced to a body lumen and is well known in the art. Typically, a stent is implanted in a blood vessel at the site of a stenosis or aneurysm endoluminally, by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Particular problems arise from stenosis in the superficial femoral artery (SFA). In combating problems associated with the SFA, stents can be placed therein. Any stent placed in the SFA must have a great deal of flexibility so as to cope with the repeated bending of the artery and also be resistant to fatigue.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a stent comprising a first end portion, a second end portion, and a middle therebetween. The first end portion and the second end portion each comprise strut columns which are interconnected to one another. The interconnected strut columns comprise peaks and valleys. The peaks and valleys of the interconnected strut columns of the first end portion have a repeating pattern and the peaks and valleys of the interconnected strut columns of the second end portion have a repeating pattern. The repeating pattern of the first end portion is different from the repeating pattern of the second end portion.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
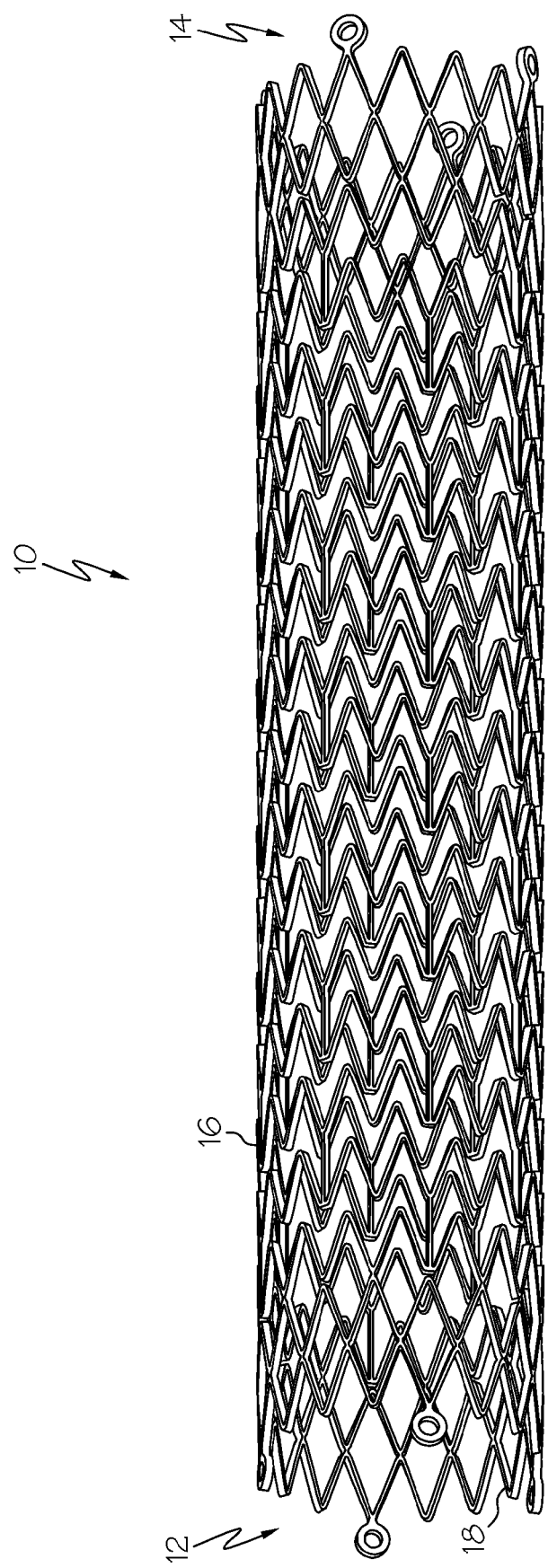
FIG. 1 is a perspective view of an embodiment of a stent 10.

While this invention may be embodied in many different forms, there are described in detail herein specific embodiments. This description is an exemplification of the principles of the invention and is not intended to limit it to the particular embodiments illustrated.

For the purposes of this disclosure, like reference numerals in the figures shall refer to like features unless otherwise indicated.

In at least one embodiment, for example as shown in FIG. 1, a stent 10 comprises a tubular structure having a proximal end 12 and a distal end 14 and an outer surface 16 and an inner surface 18. The stent 10 has an unexpanded configuration and an expanded configuration.

Figure 2:
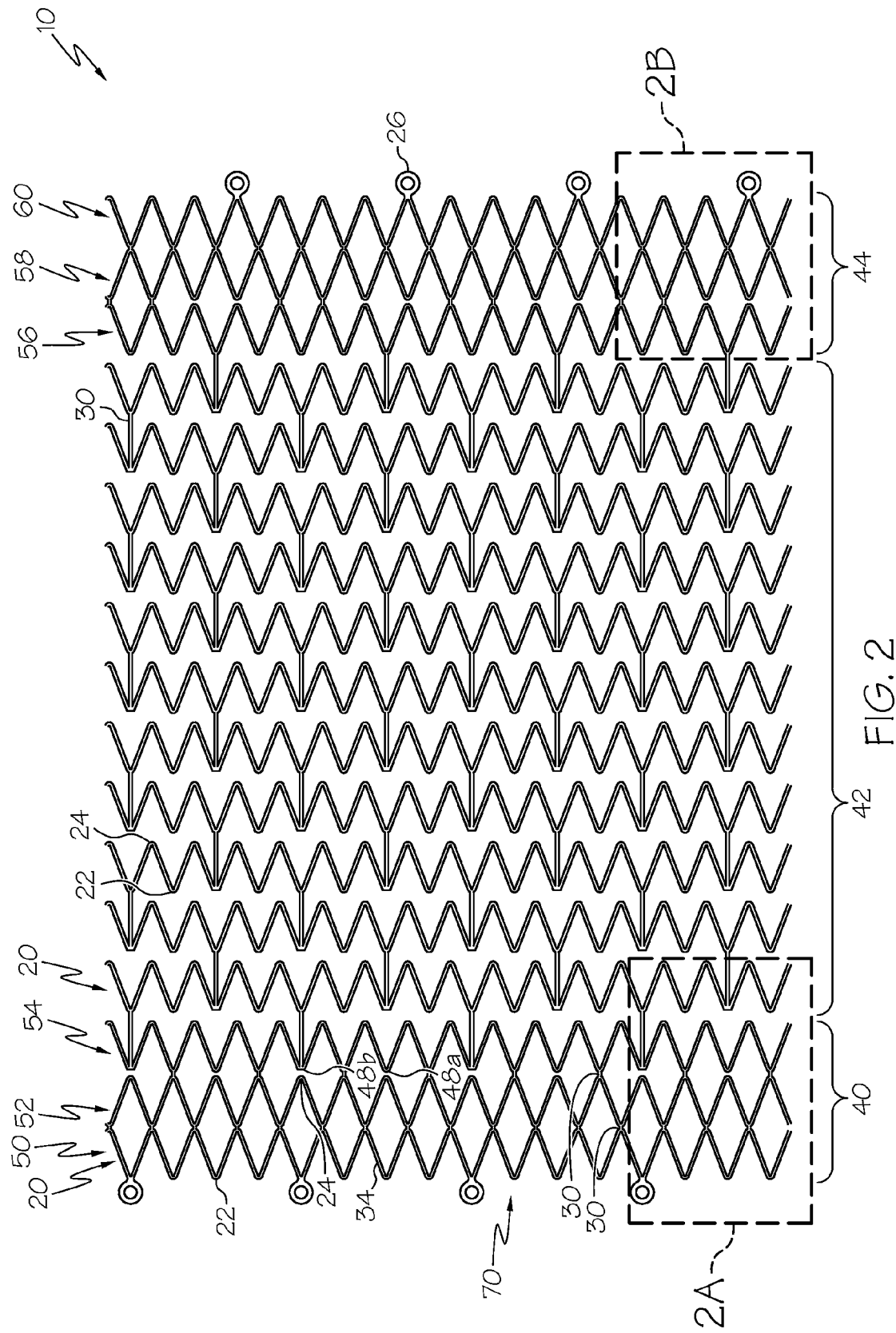
FIG. 2 is a planar view of the embodiment of the stent of FIG. 1.
Figure 2B:
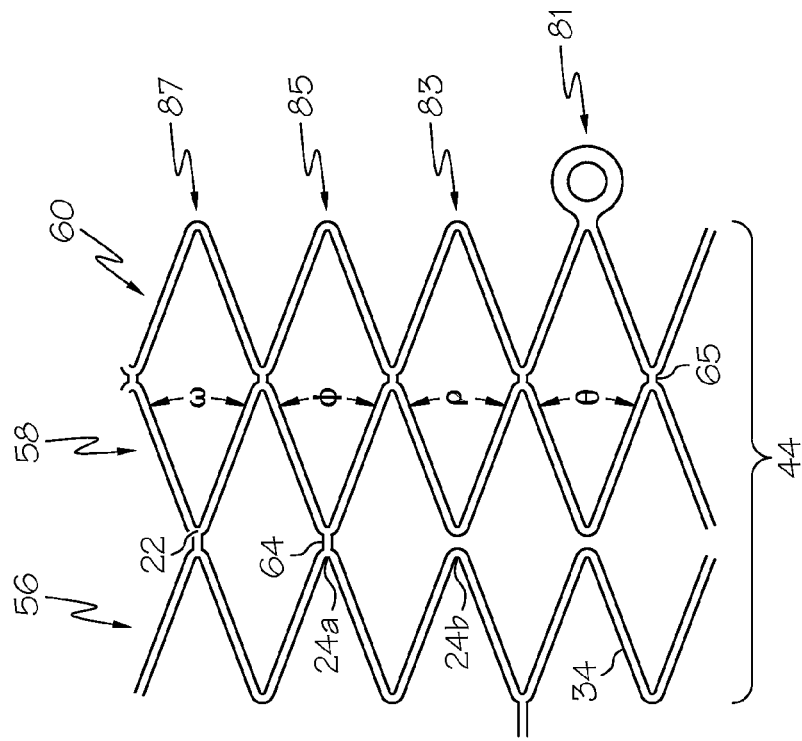
FIG. 2B is a detailed view of the embodiment of the stent of FIGS. 1 and 2.
Figure 2A:
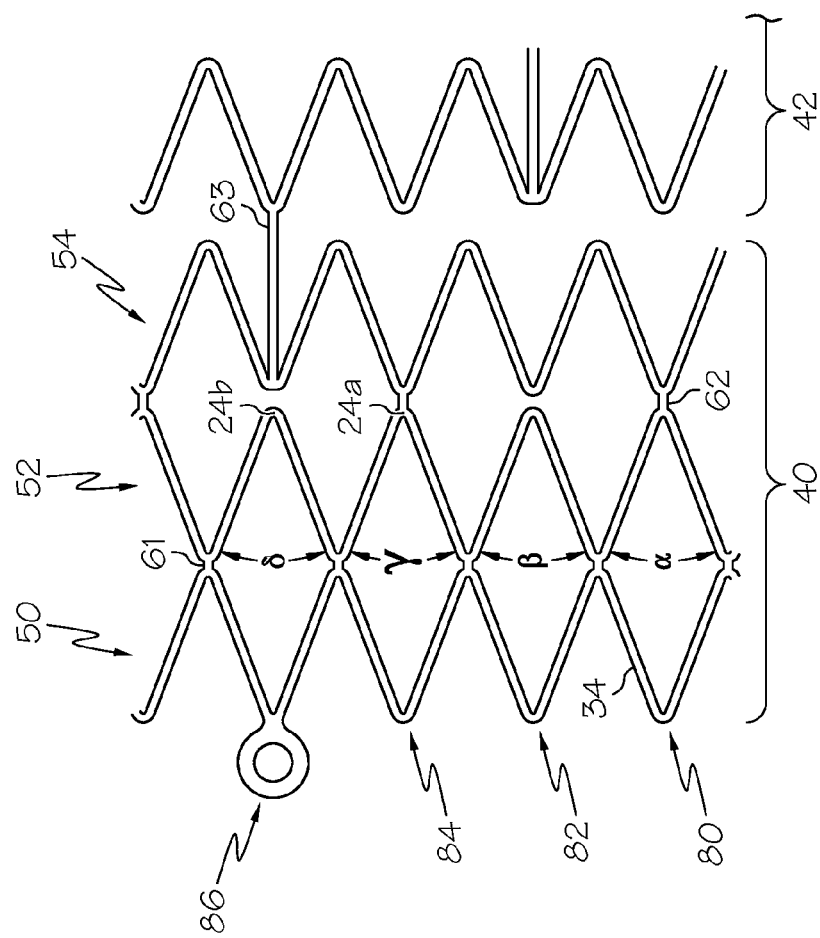
FIG. 2A is a detailed view of the embodiment of the stent of FIGS. 1 and 2.
Figure 3:
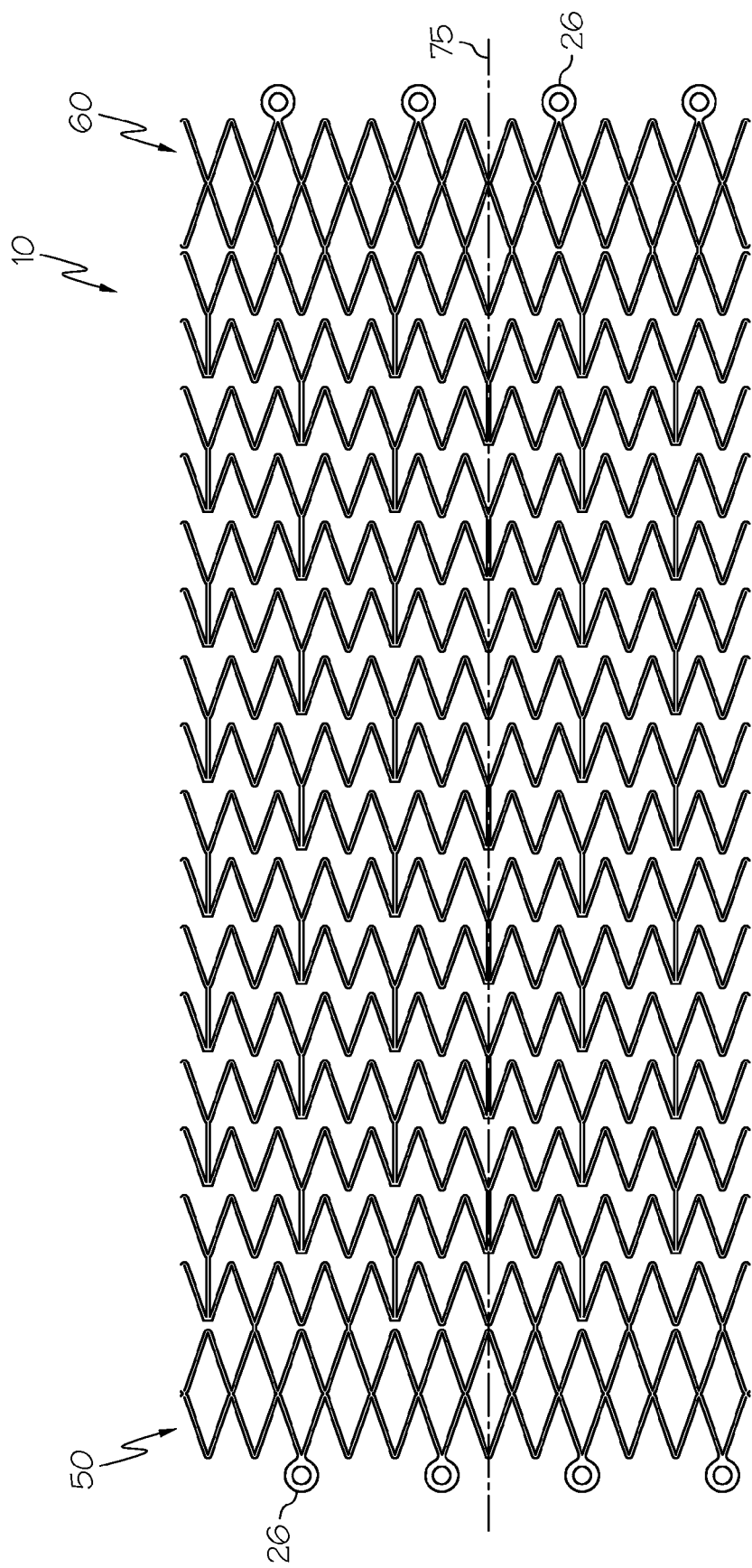
FIG. 3 is a planar view of an embodiment of a stent 10.
Figure 4:
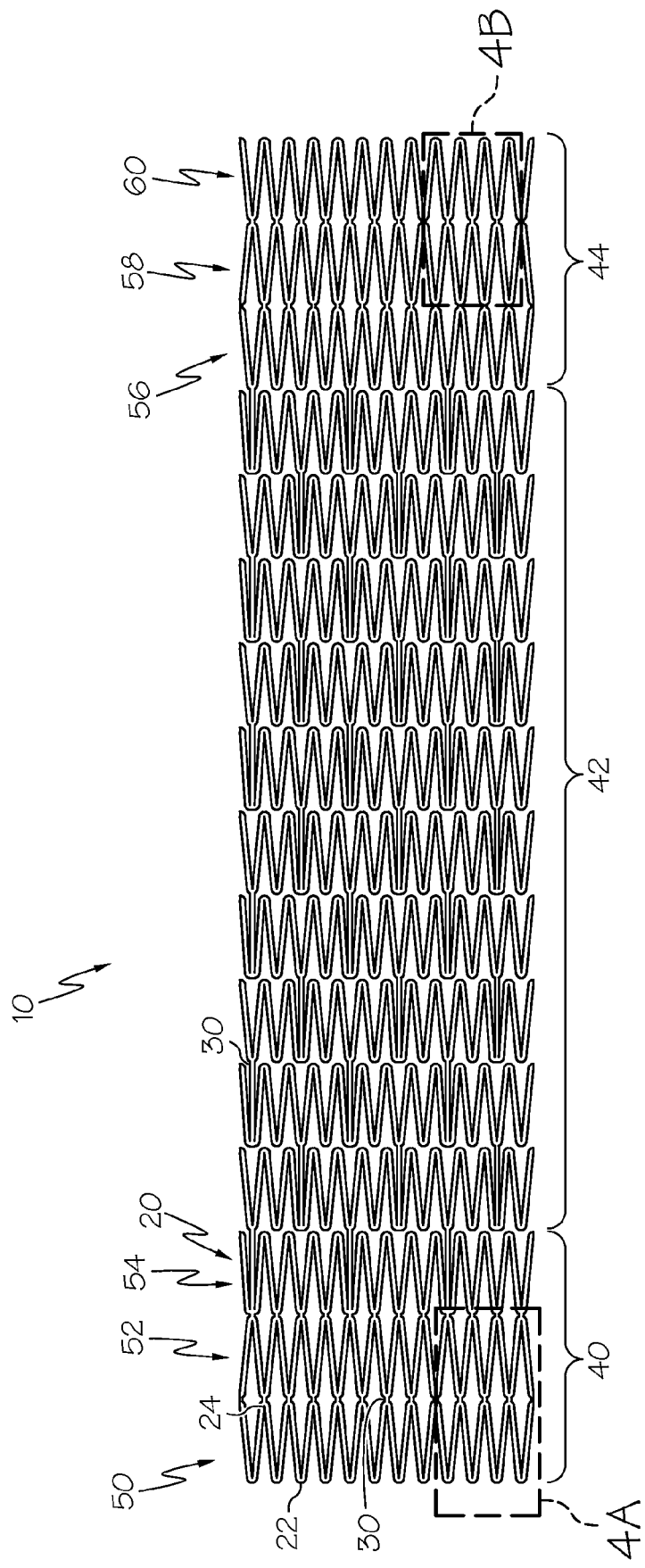
FIG. 4 is a planar view of an embodiment of a stent 10.
Figure 4B:
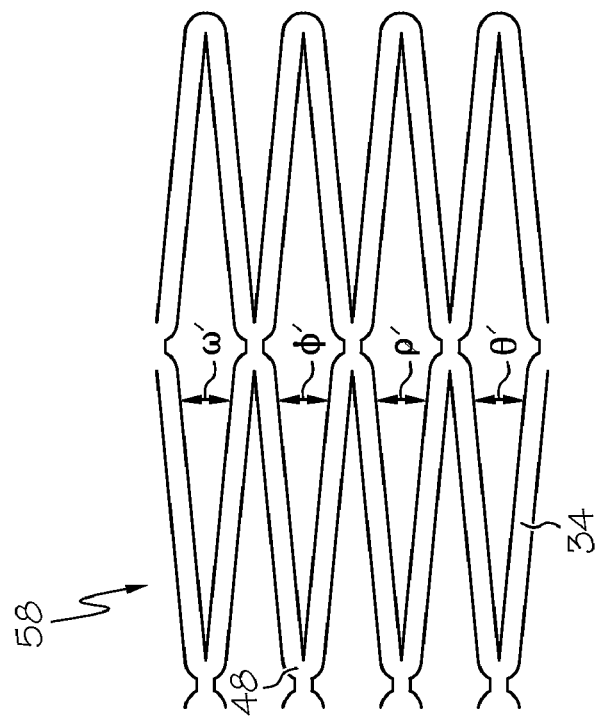
FIGS. 4A and 4B are detailed views of the embodiment of the stent of FIG. 4.
Figure 4A:
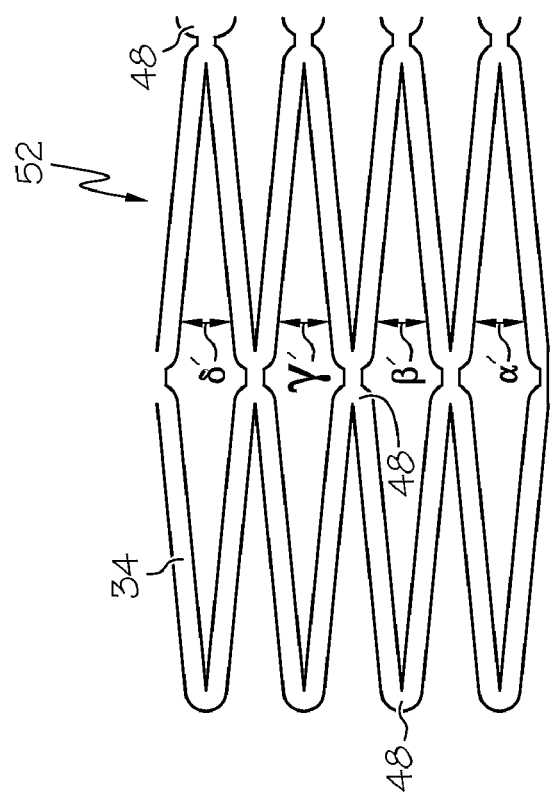

FIGS. 1, 2, 2A, 2B, and 3, show a stent 10, or portions thereof, in an expanded configuration. FIGS. 4, 4A, and 4B show a stent 10, or portions thereof, in an "as cut" configuration. "As-cut" means that the stent is in a stable configuration, prior to any polishing, expansion, crimping, or placement on a deployment catheter, for example.

Turning to FIG. 2, a planar view of the stent 10 of FIG. 1 is shown. In some embodiments, the stent 10 comprises a plurality of serpentine bands or strut columns 20. In some embodiments, the strut columns 20 comprise a plurality of peaks 22 and valleys 24. The peaks 22 of a strut column 20 are proximal to the valleys 24. Adjacent strut columns 20 are connected one to another. In some embodiments, the valleys 24 of a strut column 20 are aligned along a common circumference, for example as shown in FIG. 2. Moreover, in some embodiments, the peaks 22 of a strut column 20 are aligned along a common circumference, also as shown in FIG. 2, for example.

The stent 10 further comprises a proximal end portion 40 a distal end portion 44 and a middle portion 42 between the proximal end portion 40 and the distal end portion 44. In some embodiments, the proximal end portion 40 comprises three strut columns 20. In some embodiments, the distal end portion 44 comprises three strut columns 20. In some embodiments, the middle portion 42 comprises one or more strut columns 20. Strut columns 20 can be alternatively be referred to as serpentine bands.

In some embodiments, the proximal end portion 40 comprises a first strut column 50, a second strut column 52, and a third strut column 54. In some embodiments, the first strut column 50 is disposed at the proximal end 12 of the stent 10. The second strut column 52 is disposed distal to the first strut column 50 and the third strut column 54 is disposed distal to the first and second strut columns 50, 52.

In some embodiments, the valleys 24 of the first strut column 50 are connected to the peaks 22 of the second strut column 52. In some embodiments, each valley 24 of the first strut column 50 is connected to a peak 22 of the second strut column 52.

In some embodiments, valleys 24 of the second strut column 52 are connected to peaks 22 of the third strut column 54. In some embodiments, half of the valleys 24 of the second strut column 52 are connected to peaks 22 of the third strut column 54. As shown in FIG. 2, every other valley 24 of the second strut column 52 is connected to a peak 22 of the third strut column 54. The valleys 24 thereby follow a repeating pattern of connected valleys 24a and unconnected valleys 24b. The repeating pattern of connected valleys 24a and unconnected valleys 24b comprises one connected valley 24a followed by one unconnected valley 24b, at which point the repeating pattern repeats. Thus, the second strut column 52 has a connected valley 24a followed by an unconnected valley 24b, which is followed by a connected valley 24a followed by an unconnected valley 24b, and so forth along the length of the second strut column 52.

In some embodiments, peaks 22 of the third strut column 54 are connected to the middle portion 42. In some embodiments, one-fourth of the peaks 22 of the third strut column 54 are connected to the middle portion 42. As shown in FIG. 2, every fourth peak 22 of the third strut column 54 is connected to the middle portion 42. In some embodiments, half as many peaks 22 of the third strut column 54 are connected to the middle portion 42 as peaks 22 of the third strut column 54 are connected to valleys 24 of the second strut column 52. The peaks 22 of the third strut column 54 thereby follow a repeating pattern of peaks 22 connected to the middle portion 42 and peaks 22 unconnected to the middle portion 42. The repeating pattern comprises one peak 22 connected to the middle portion 42 followed by three peaks 22 which are unconnected to the middle portion 42, at which point the pattern repeats with a peak 22 connected to the middle portion 42 followed by three peaks 22 which are unconnected to the middle portion 42.

In some embodiments, the distal end portion 44 comprises a fourth strut column 56, a fifth strut column 58, and a sixth strut column 60. In some embodiments, the sixth strut column 60 is disposed at the distal end 14 of the stent 10. The fifth strut column 58 is disposed proximal to the sixth strut column 60 and the fourth strut column 56 is disposed proximal to the sixth and fifth strut columns 60, 58.

In some embodiments, peaks 22 of the fourth strut column 56 are connected to the middle portion 42. In some embodiments, one-fourth of the peaks 22 of the fourth strut column 56 are connected to the middle portion 42. In some embodiments, one-fourth of the total number of peaks 22 of the fourth strut column 56 are connected to peaks 22 of the distal most strut column 20 of the middle portion 42. As shown in FIG. 2, every fourth peak 22 of the fourth strut column 56 is connected to the middle portion 42. The peaks 22 of the fourth strut column 56 thereby follow a repeating pattern of connected and unconnected peaks 22. The repeating pattern of connected and unconnected peaks comprises one connected peak 22 followed by three unconnected peaks 22, at which point the repeating pattern repeats. Thus, the fourth strut column 56 has a connected peak followed by an unconnected peak, which is followed by two additional unconnected peaks, which is followed by a connected peak, and so fourth along the length of the fourth strut column 56.

In some embodiments, the peaks 22 of the fifth strut column 58 are connected to valleys 24 of the fourth strut column 56. In some embodiments, half of the peaks 22 of the fifth strut column 58 are connected to valleys 24 of the fourth strut column. In some embodiments, twice as many peaks 22 of the fifth strut column 58 are connected to valleys 24 of the fourth strut column 56 as peaks 22 of the fourth strut column 56 are connected to peaks 22 of the distal most strut column 20 of the middle portion 42. As shown in FIG. 2, the peaks 22 of the of the fifth strut column 58 follow a repeating pattern of connected peaks and unconnected peaks 22. The repeating pattern of connected and unconnected peaks 22 comprises two connected peaks followed by two unconnected peaks, at which point the repeating pattern repeats. Thus, the fifth strut column 58 has a connected peak followed by another connected peak, which is followed by an unconnected peak and another unconnected peak, and so forth along the length of the fifth strut column 58.

In some embodiments, the peaks 22 of the sixth strut column 60 are connected to the valleys 24 of the fifth strut column 58. In some embodiments, each peak 24 of the sixth strut column 60 is connected to a valley 24 of the fifth strut column 58.

In some embodiments, the middle portion comprises as many strut columns as are desired to achieve the necessary length of the stent as dictated by the anatomy to be treated. In some embodiments, the number of columns ranges from 1 to 100. As a non-limiting example, the middle portion 42 can comprise 3, 4, 11, 13, 14, 20, 23, 29, 32, 33, 37, 42, 43, 46, 51, 53, 59, 66, 68, 72, 80, 82, 90, or 92 strut columns, depending upon the desired length of the stent. Adjacent strut columns of the middle portion 42 are attached to each other with a plurality of connecting struts 30.

In some embodiments, the connecting struts 30 connect peaks 22 of immediately adjacent strut columns 20 of the middle portion 42. As shown in FIG. 2, every other peak 22 of the strut columns of the middle portion 42 has a connecting strut 30 connected thereto. Moreover, every fourth peak of the strut columns of the middle portion 42 has a connecting strut 30 extending distally therefrom. Every fourth peak of the strut columns of the middle portion 42 has a connecting strut 30 extending proximally therefrom. Thus, the strut columns 20 of the middle portion comprise a repeating pattern of connected and unconnected peaks 22. The repeating pattern comprises an unconnected peak followed by a connected peak having a connecting strut 30 extending proximally from the peak followed by an unconnected peak followed by a connected peak having a connecting strut 30 extending distally from the peak. This repeating pattern of connected and unconnected peaks then repeats. In some embodiments, the repeating pattern repeats four times. Consequently, in some embodiments, strut columns 20 of the stent 10 each comprise sixteen peaks 22 and sixteen valleys 24. In some embodiments, the repeating pattern repeats three times. The stent 10 can also comprise any suitable number of repeats of the repeating pattern, for example between two and ten times, depending upon the desired diameter and configuration of the stent.

In some embodiments, the peaks 22 of the third strut column 54 connected to the middle portion 42 are unconnected to valleys 24 of the second strut column. In this way, peaks 22 of the third strut column 54 which are connected to the middle portion 42 via connectors 30 are circumferentially offset from the peaks 22 of the third strut column 54 which are connected to valleys 24 of the second strut column 52.

In some embodiments, the peaks 22 of the fourth strut column 56 connected to the middle portion 42 are disposed circumferentially between unconnected valleys 24 of the fourth strut column 56. In some embodiments, each peak 22 of the fourth strut column 56 which is connected to the middle portion 42 via connectors 30 circumferentially bisects the unconnected valleys 24b of the fourth strut column 56.

In addition to having strut columns 20, the stent 10 comprises a plurality of strut rows 70. Each strut row 70 comprises pairs of strut members 34. The pairs of strut members 34 form either a peak 22 or a valley 24.

As shown in FIG. 2A, a detailed view of a portion of the stent 10 is shown, including a portion of the proximal end portion 40. The detailed view shown in FIG. 2A depicts an embodiment of the stent 10 in an expanded and polished configuration, prior to crimping or placement on a deployment catheter, for example. As shown in FIG. 2A, adjacent strut members 34 of each peak 22 and valley 24 are angularly offset from one another. The strut members 34 of the valleys 24 of the second strut column 52 are angularly offset by angles $\alpha$, $\beta$, $\gamma$, and $\delta$, respectively. Angle $\alpha$ is defined as the angle between strut members 34 of the valley 24 of the second strut column 52 of first strut row 80. Angle $\beta$ is defined as the angle between strut members 34 of the valley 24 of the second strut column 52 of third strut row 82. Angle $\gamma$ is defined as the angle between strut members 34 of the valley 24 of the second strut column 52 of fifth strut row 84. Finally, angle $\delta$ is defined as the angle between strut members 34 of the valley 24 of the second strut column 52 of seventh strut row 86. It will be appreciated that in some embodiments, the sequence of angles $\alpha$, $\beta$, $\gamma$, and $\delta$ repeats along the strut column, for example as: $\alpha$, $\beta$, $\gamma$, $\delta$, $\alpha$, $\beta$, $\gamma$, $\delta$, $\alpha$, $\beta$, $\gamma$, $\delta$, etc.

In some embodiments, angle $\alpha$ is 33 degrees, angle $\beta$ is 33 degrees, angle $\gamma$ is 35 degrees, and angle $\delta$ is 36 degrees. In some embodiments, angle $\alpha$ is 36 degrees, angle $\beta$ is 36 degrees, angle $\gamma$ is 38 degrees, and angle $\delta$ is 40 degrees. In some embodiments, angle $\alpha$ is 39 degrees, angle $\beta$ is 39 degrees, angle $\gamma$ is 41 degrees, and angle $\delta$ is 43 degrees. In some embodiments, angle $\alpha$ is 40 degrees, angle $\beta$ is 40 degrees, angle $\gamma$ is 42 degrees, and angle $\delta$ is 44 degrees. In some embodiments, angle $\alpha$ is 41 degrees, angle $\beta$ is 41 degrees, angle $\gamma$ is 43 degrees, and angle $\delta$ is 44 degrees.

In some embodiments, angle $\beta$ is equal to angle $\alpha$. In some embodiments, angle $\gamma$ is equal to angle $\beta$ plus 2 degrees. In some embodiments, angle $\delta$ is equal to angle $\gamma$ plus 1 degree. In some embodiments, angle $\delta$ is equal to angle $\gamma$ plus 2 degrees. In some embodiments, angle $\delta$ is equal to angle $\alpha$ and/or $\beta$ plus 3 degrees. In some embodiments, angle $\delta$ is equal to angle $\alpha$ and/or $\beta$ plus 4 degrees.

Turning to FIG. 2B, a detailed view of a portion of the stent 10 is shown, including a portion of the distal end portion 44. As shown in FIG. 2B, strut members 34 of each peak 22 and valley 24 are angularly offset from one another. The strut members 34 of the peaks 22 of the fifth strut column 58 are angularly offset by angles $\theta$, $\rho$, $\phi$, and $\omega$, respectively. Angle $\theta$ is defined as the angle between strut members 34 of the peak 22 of the fifth strut column 58 of second strut row 81. Angle $\rho$ is defined as the angle between strut members 34 of the peak 22 of the fifth strut column 58 of the fourth strut row 83. Angle $\phi$ is defined as the angle between strut members 34 of the peak 22 of the fifth strut column 58 of the sixth strut row 85. Angle $\omega$ is defined as the angle between strut members 34 of the peak 22 of the fifth strut column 58 of the seventh strut row 87. It will be appreciated that in some embodiments, the sequence of angles $\theta$, $\rho$, $\phi$, and $\omega$ repeats along the strut column, for example as: $\theta$, $\rho$, $\phi$, $\omega$, $\theta$, $\rho$, $\phi$, $\omega$, $\theta$, $\rho$, $\phi$, $\omega$, etc.

In some embodiments, for example as shown in FIG. 2, the second strut row 81 shares strut members 34 with the first strut row 80 and the third strut row 83. Thus, in some embodiments, second strut row 81 is partially overlapping with first strut row 80 and third strut row 82. Similarly, third strut row 82 is partially overlapping with second strut row 81 and fourth strut row 83. The fourth, fifth, sixth, seventh, and eighth strut rows (83, 84, 85, 86, 87) are correspondingly situated.

In some embodiments, angle $\theta$ is 34 degrees, angle $\rho$ is 34 degrees, angle $\phi$ is 34 degrees, and angle $\omega$ is 34 degrees. In some embodiments, angle $\theta$ is 38 degrees, angle $\rho$ is 38 degrees, angle $\phi$ is 38 degrees, and angle $\omega$ is 38 degrees. In some embodiments, angle $\theta$ is 41 degrees, angle $\rho$ is 41 degrees, angle $\phi$ is 41 degrees, and angle $\omega$ is 41 degrees. In some embodiments, angle $\theta$ is 42 degrees, angle $\rho$ is 42 degrees, angle $\phi$ is 42 degrees, and angle $\omega$ is 42 degrees. In some embodiments, angles $\theta$, $\rho$, $\phi$, and $\omega$ are all the same.

In some embodiments, the stent 10 comprises sixteen (16) non-overlapping rows 70, for example as shown in FIG. 2, for use in vessels approximately 5-9 millimeters in diameter. In some embodiments, the stent 10 comprises twelve (12) non-overlapping rows 70, for example as shown in FIG. 3, for use in vessels approximately 3-7 millimeters in diameter. In some embodiments, the stent 10 comprises eight (8) non-overlapping rows 70, for example, to be used in vessels approximately 2-5 millimeters in diameter. In some embodiments, the stent 10 comprises twenty (20) non-overlapping rows 70, for example, to be used in vessels approximately 8-14 millimeters in diameter. In some embodiments, the stent 10 comprises twenty-four (24) non-overlapping rows 70, for example, to be used in vessels approximately 12-20 millimeters in diameter.

In some embodiments, for example as shown in FIG. 2, strut columns 20 comprise strut pair nodes 48. In some embodiments, strut pair nodes 48 are unevenly distributed around the circumference of the stent 10. For example, strut pair nodes 48b having a connector 30 between circumferentially adjacent strut members 34 of a peak 22 can be wider than strut pair nodes 48a not having a connector between circumferentially adjacent strut members 34 of peaks 22 and valleys 24. Thus, in some embodiments, the spacing of strut pair nodes 48 of a strut column 20 varies along the length of the strut column 20. In some embodiments, the spacing of the strut pair nodes 48 around the circumference of the stent 10 follows a repeating pattern. In some embodiments, the spacing of the nodes 48 is determined by angles $\alpha$, $\beta$, $\gamma$, $\delta$, and $\theta$, $\rho$, $\phi$, $\omega$, respectively.

In some embodiments, the first and second strut columns 50, 52 are connected to one another with X connecting struts 30 and the second and third strut columns 52, 54 are connected to one another with Y connecting struts 30. In some embodiments, Y is ½(X). In some embodiments, the proximal most strut column 20 of the middle portion 42 is connected to the third strut column 54 with Z connecting struts 30. In some embodiments, Z is ½(Y). In some embodiments, the fifth and sixth strut columns 58, 60 are connected to one another with R connecting struts 30 and the fourth and fifth strut columns 56, 58 are connected to one another with V connecting struts 30. In some embodiments V is ½(R). In some embodiments, the distal most strut column 20 of the middle portion 42 is connected to the fourth strut column 56 with W connecting struts 30. In some embodiments, W is ½(V).

In some embodiments, strut members 34 of a particular strut column are the same length. In some embodiments, strut members 34 of a particular portion (e.g., proximal end portion 40, middle portion 42, distal end portion 44) are the same length. In some embodiments, all of the strut members 34 of the stent 10 are the same length. In some embodiments, the length of the struts is between approximately 0.045-0.120 inches, and in some embodiments, is 0.05 and 0.09 inches.

In some embodiments, strut members 34 of a particular strut column are the same width. In some embodiments, strut members 34 of a particular portion (e.g., proximal end portion 40, middle portion 42, distal end portion 44) are the same width. In some embodiments, all of the strut members 34 of the stent 10 are the same width. In some embodiments, the width of the struts is between approximately 0.002 and 0.007 inches, and in some embodiments, is 0.003-0.005 inches, for example 0.0039 inches.

In some embodiments, the first strut column 50 is connected to the second strut column 52 with a plurality of connecting struts 30. In some embodiments, the connecting struts 30 connecting the first strut column 50 to the second strut column 52 comprise first connecting struts 61.

In some embodiments, the second strut column 52 is connected to the third strut column 54 with a plurality of connecting struts 30. In some embodiments, the connecting struts 30 connecting the second strut column 52 to the third strut column 54 comprise second connecting struts 62.

In some embodiments, the third strut column 54 is connected to a strut column of the middle portion 42 with a plurality of connecting struts 30. In some embodiments, the connecting struts 30 connecting the third strut column 54 to the middle portion 42 comprise third connecting struts 63.

In some embodiments, the fourth strut column 56 is connected to a strut column of the middle portion 42 with a plurality of connecting struts 30. In some embodiments, the connecting struts 30 connecting the fourth strut column 56 to the middle portion 42 comprise third connecting struts 63.

In some embodiments, the fifth strut column 58 is connected to the fourth strut column 56 with a plurality of connecting struts 30. In some embodiments, the connecting struts 30 connecting the fifth strut column 56 to the fourth strut column 54 comprise fourth connecting struts 64.

In some embodiments, the sixth strut column 60 is connected to the fifth strut column 58 with a plurality of connecting struts 30. In some embodiments, the connecting struts 40 connecting the sixth strut column 60 to the fifth strut column 58 comprise fifth connecting struts 65.

In some embodiments, the first connecting struts 61 have the same length as the fifth connecting struts 65. In some embodiments, the second connecting struts 62 have the same length as the fourth connecting struts 64. In some embodiments, the first and fifth connecting struts 61, 65 are shorter than the second, third, and fourth connecting struts 62, 63, 64, respectively. In some embodiments, the second and fourth connecting struts 62, 64 are shorter than the third connecting struts 63.

In some embodiments, the length of the first connecting struts 61 is less than 0.005 inches. In some embodiments, the length of the first connecting struts 61 is 0.002 inches.

In some embodiments, the length of the second connecting struts 62 is between approximately 0.002 and 0.010 inches, and in some embodiments, between 0.003 and 0.005 inches.

In some embodiments, the length of the third connecting struts 63 is between approximately 0.045 and 0.120 inches. In some embodiments, the length of the third connecting struts 63 is approximately 0.06-0.07 inches. In some embodiments, the length of the third connecting struts 63 is greater than or equal to the length of strut members 34.

In some embodiments, the length of the fourth connecting struts 64 is between approximately 0.002 and 0.010 inches, and in some embodiments, between 0.003 and 0.005 inches.

In some embodiments, the length of the fifth connecting struts 65 is less than 0.005 inches. In some embodiments, the length of the first connecting struts 61 is 0.002 inches.

In some embodiments, the width of the connecting struts 61, 62, 63, 64, 65 is between approximately 0.002 and 0.007 inches, and in some embodiments, between approximately 0.0035 and 0.0045 inches. In some embodiments, all of the first connecting struts 61 have the same width. In some embodiments, all of the second connecting struts 62 have the same width. In some embodiments, all of the third connecting struts 63 have the same width. In some embodiments, all of the fourth connecting struts 64 have the same width. In some embodiments, all of the fifth connecting struts 65 have the same width. In some embodiments, all of the connecting struts 30 of the stent 10 have the same width.

In some embodiments, the thickness of the strut members 34 is between approximately 0.004 and 0.017 inches, and in some embodiments, between 0.007 and 0.009 inches. In some embodiments, the thickness of the connecting struts 30 is between approximately 0.004 and 0.017 inches, and in some embodiments, between 0.007 and 0.009 inches. The thickness is the distance from the inner surface 18 to the outer surface 16.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments, the stent 10 comprises a radiopaque marker housing 26. In some embodiments, the stent 10 comprises a plurality of radiopaque marker housings 26. In some embodiments, the stent 10 has a plurality of radiopaque marker housings 26 extending proximally from the proximal end portion 40 and distally from the distal end portion 44. As shown for example in FIG. 2, the radiopaque marker housings 26 extending from the proximal end portion 40 extend from the peaks 22. The radiopaque marker housings 26 extending from the distal end portion 44 extend from the valleys 24.

In some embodiments, the stent comprises four radiopaque marker housings 26 extending from the proximal end portion 40 and four radiopaque marker housings 26 extending from the distal end portion 44. The stent 10 can also comprise any suitable number of radiopaque marker housings, for example between 1 and 20.

Moreover, in some embodiments, radiopaque marker housings 26 are placed on every fourth peak 22 of the first strut column 50. In some embodiments, the radiopaque marker housings 26 are circumferentially aligned with the connecting struts 30 extending from the peaks 22 of the third strut column 54 to the peaks 22 of the adjacent strut column of the middle portion 42. In some embodiments, radiopaque marker housings 26 are placed on every fourth valley 24 of the sixth strut column 60. Thus, the stent 10 can have the same number of radiopaque marker housings 26 on each of the proximal and distal ends 12, 14 as the number of connecters 30 extending between adjacent strut columns 20 of the middle portion 42. For example, each of the proximal and distal ends 12, 14 can comprise four radiopaque marker housings 26 and each of the adjacent strut columns 20 of the middle portion 42 have four connectors 30 extending therebetween. In some embodiments, the stent 10 can have fewer or more radiopaque marker housings 26 on each of the proximal and/or distal ends 12, 14 than the number of connectors 30 extending between adjacent strut columns 20 of the middle portion 42.

In some embodiments, for example as shown in FIG. 3, radiopaque marker housings 26 are placed on every third peak 22 of the first strut column 50. In some embodiments, the radiopaque marker housings 26 are placed on every third valley 24 of the sixth strut column 60. In some embodiments, the radiopaque marker housings 26 are evenly spaced around the circumference of the stent. The radiopaque marker housings 26 can also be placed in any other suitable configuration, for example in an unevenly spaced configuration.

Figure 2C:
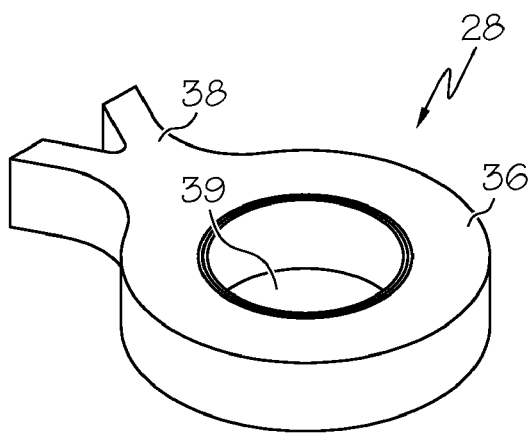
FIGS. 2C-2F are detailed views of a radiopaque marker housing of the stent of FIGS. 1 and 2.
Figure 2D:
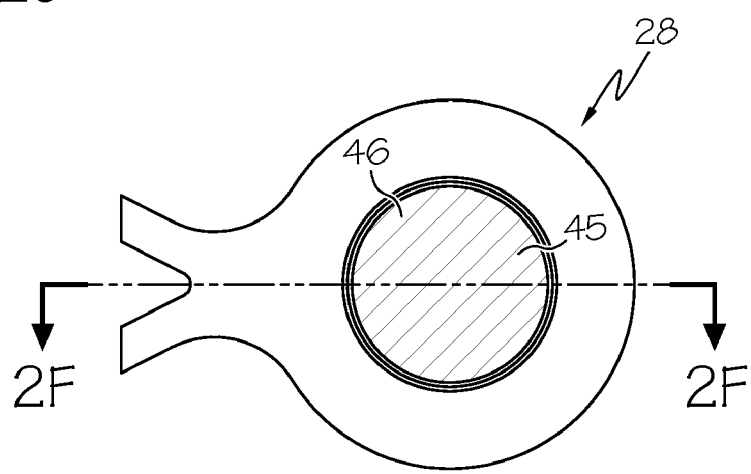

In some embodiments, a portion of the radiopaque marker housings 26 is annularly shaped, for example as shown in FIGS. 2C and 2D. The annularly shaped radiopaque marker housings 26 can be alternatively referred to as "paddles" 28. The paddles 28 comprise a ring portion 36 and a stem 38. The ring portion 36 defines an opening 39, in which radiopaque material 45 can be disposed. In some embodiments, the radiopaque material is tantalum. The radiopaque material 45 can further comprise any suitable material, for example gold, iridium, platinum, tantalum, and combinations thereof.

In some embodiments, a radiopaque insert 46 of radiopaque material 45 is disposed within the opening 39. In some embodiments, the radiopaque insert 46 is swaged or pressed into the opening 39. The radiopaque insert 46 can also be inserted into opening 39 in any other suitable manner. In some embodiments, the radiopaque insert is inserted into the opening according to the process shown and described in U.S. Pat. No. 7,243,408 to Vietmeier, which is herein incorporated by reference.

Figure 2E:
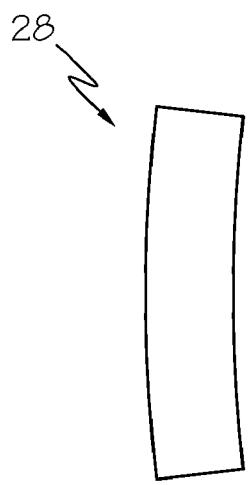
Figure 2F:
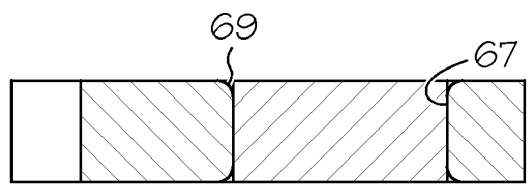

Moreover, in some embodiments, the opening 39 has a cylindrical cross section 67, for example as shown in FIG. 2F. In some embodiments, the opening 39 has a radius 69 on one or more of the intersecting surfaces of the opening 39 and the ring portion 36.

The stem 38 extends away from the peak 22 or valley 24 of the proximal end portion 40 or distal end portion 44 and connects the paddle 28 to the remainder of the stent 10. As shown for example in FIG. 2E, the paddle 28 is curved in accordance with the curvature of the stent inner and outer surfaces 18, 16. Examples of other suitable radiopaque marker housings are shown and described in US Publication No. 2008/0288046 to Hemerick et al., which is herein incorporated by reference.

Turning now to FIG. 3, in some embodiments, the stent 10 comprises a plurality of radiopaque marker housings 26 disposed on every third peak 22 of the first strut column 50 and every third valley 24 of the sixth strut column 60.

In some embodiments, for example as shown in FIG. 3, the repeating pattern of connected and unconnected peaks 22 and valleys 24 repeats three times. Consequently, in some embodiments, strut columns 20 of the stent 10 each comprise twelve peaks 22 and twelve valleys 24.

In some embodiments, the middle portion 42 is capable of expanding from an unexpanded configuration to an expanded configuration without longitudinal foreshortening, for example due to the arrangement of peak-to-peak connecting struts 30. In some embodiments, the middle portion 42 is symmetrical across a longitudinal axis 75 (e.g., FIG. 3).

In some embodiments, the expansion characteristics of the proximal end portion 40 are different than the expansion characteristics of the distal end portion 44 of the stent 10. In some embodiments, the distal end portion 44 can be partially deployed while retaining the proximal end portion 40 in an undeployed configuration. In some embodiments, the distal end portion 44 of the stent 10 is suited for "flowering" during stent deployment. In this way, in some embodiments, the distal end portion 44 of the stent 10 is configured to expand radially upon partial deployment from a catheter or sheath without radial expansion of the middle portion 42 and proximal end portion 40. Thus, in some embodiments, the distal end portion 44 can be at least partially expanded while the middle portion 42, or a portion thereof, and the proximal end portion 40 remain in an unexpanded configuration within the catheter or sheath. In some embodiments, the flowering stent is used to drag back a partially deployed stent to the desired target location within the lumen and improve accuracy in stent placement. In some embodiments, either end portion 40, 44 is capable of "flowering," for example, during deployment. In some embodiments, both end portions 40, 44 are capable of flowering. In some embodiments, the proximal end portion 40 and/or distal end portion 44 can flare or taper. In some embodiments, the stent 10 can taper from one end to the other end.

In some embodiments, the stent 10 is loaded into a catheter such that the distal end portion 44 of the stent 10 is disposed at or near the distal end of the catheter and the proximal end portion 40 is closer to the proximal end of the catheter. In this way, the stent can be deployed as described above. The stent 10 can also be loaded into the catheter in the opposite direction.

In some embodiments, the peaks and valleys of the first strut column 50 are out of phase with the peaks and valleys of the second strut column 52. In some embodiments, the peaks and valleys of the second strut column 52 are out of phase with the peaks and valleys of the third strut column 54. In some embodiments, the peaks and valleys of the fourth strut column 56 are out of phase with the peaks and valleys of the fifth strut column 58. In some embodiments, the peaks and valleys of the fifth strut column 58 are out of phase with the peaks and valleys of the sixth strut column 60.

In some embodiments, the peaks and valleys of the first, third, fourth, and sixth strut columns 50, 54, 56, 60, respectively, are all in phase with one another. In some embodiments, the second and fifth strut columns 52, 58 are in phase with one another.

In some embodiments, for example as shown in FIG. 4, a stent 10 comprises a proximal end portion 40, a distal end portion 44, and a middle portion 42 therebetween. As shown, the proximal end portion 40 comprises three strut columns 20 and the distal end portion 44 comprises three strut columns 20.

In some embodiments, the stent 10 comprises a first strut column 50, a second strut column 52, and a third strut column 54. Each of the first, second, and third strut columns 50, 52, 54 comprises a plurality of alternating peaks 22 and valleys 24. The peaks 22 of the second strut column 52 are connected to the valleys 24 of first strut column 50. In some embodiments, each peak 22 of the second strut column 52 is connected to a valley 24 of the first strut column 50. In some embodiments, the peaks 22 of the third strut column 54 are connected to the valleys 24 of the second strut column 52. In some embodiments, each peak 22 of the third strut column 54 is connected to a valley 24 of the second strut column.

In some embodiments, the stent 10 comprises a fourth strut column 56, a fifth strut column 58, and a sixth strut column 60. Each of the fourth, fifth, and sixth strut columns 56, 58, 60 comprises a plurality of alternating peaks 22 and valleys 24. The valleys 24 of the fourth strut column 56 are connected to peaks of the fifth strut column 58 and, in some embodiments, the valleys 24 of the fifth strut column 48 are connected to peaks 22 of the sixth strut column 60. In some embodiments, each valley 24 of the fourth strut column 56 is connected to a peak 22 of the fifth strut column 58 and each valley 24 of the fifth strut column 58 is connected to a peak 60 of the sixth strut column 60.

In some embodiments, the first strut column 50 is the same as the second strut column 52. In some embodiments, the fifth strut column 58 is the same as the sixth strut column 60.

In some embodiments, the proximal end portion 40 comprises two strut columns 20. In some embodiments, the proximal end portion 40 consists of a second strut column 52 and a third strut column 54. In some embodiments, the distal end portion 44 consists of two strut columns 20. In some embodiments, the distal end portion 44 consists of a fourth strut column 56 and a fifth strut column 58. Thus, in some embodiments, the stent 10 does not include strut columns 50 and 60.

In some embodiments, the middle portion 42 comprises a plurality of strut columns 20 which are connected one to another by at least one connecting strut 30. In some embodiments, for example as shown in FIG. 4, the strut columns 20 of the middle portion comprise a plurality of alternating peaks 22 and valleys 24. In some embodiments, the strut columns 20 are connected one to another with connecting struts 30 connecting adjacent peaks 22.

In some embodiments, the peaks 22 of the third strut column 54 are connected to peaks 22 of a strut column 20 of the middle portion 42, for example as shown in FIG. 4. In some embodiments, peaks 22 of the fourth strut column 56 are connected to peaks 22 of a strut column 20 of the middle portion 42.

In some embodiments, the connecting struts 30 connecting the second strut column 52 to the third strut column 54 are the same length as the connecting struts 30 connecting the first and second strut columns 50, 52. In some embodiments, the length of the connecting struts 30 connecting the first, second, and third strut columns 50, 52, 54 is between approximately 0.001 and 0.004 inches, and in some embodiments, is 0.002 inches. In some embodiments, the connecting struts 30 connecting the fifth strut column 58 and the sixth strut column 60 are the same length as the connecting struts connecting the fourth strut column 56 and the fifth strut column 58. In some embodiments, the length of the connecting struts 30 connecting the fourth, fifth, and sixth strut columns is between approximately 0.001 and 0.004 inches, and in some embodiments, is 0.002 inches. In some embodiments, the length of the connecting struts 30 connecting strut columns of the proximal end portion 40 is the same as the length of the connecting struts 30 connecting strut columns of the distal end portion 44.

In some embodiments, for example as shown in FIG. 4A, adjacent strut members 34 of each peak 22 and valley 24 of the second strut column 52 are angularly offset from one another. In some embodiments, strut members 34 are offset by angles $\alpha'$, $\beta'$, $\gamma'$, $\delta'$, respectively. As shown in FIG. 4A, angles $\alpha'$, $\beta'$, $\gamma'$, and $\delta'$ are all the same. In some embodiments, $\alpha'$, $\beta'$, $\gamma'$, and $\delta'$ are 40 degrees when the stent 10 is in an expanded configuration. In some embodiments, the strut pair nodes 48 of the first and second strut columns 50, 52 are equally spaced along the length of the strut column. In some embodiments, the strut pair nodes 48 of the first, second, and third strut columns 50, 52, 54 are equally spaced along the length of the respective strut column (around the circumference of the stent 10). In some embodiments, for example where the strut pair nodes 48 of the first and second strut columns 50, 52 are equally spaced, the strut pair nodes 48 of the strut pairs of the middle portion 42 are not equally spaced along the length of the respective strut column 20. In some embodiments, angles $\alpha'$, $\beta'$, $\gamma'$, and $\delta'$ between adjacent struts 34 of the second strut column 52 are all the same and angles between adjacent struts 34 of the strut columns 20 of the middle portion 42 vary. For example, in some embodiments, strut pairs of the middle portion 42 having connectors 30 attached thereto have more acute, or closed, angles than strut pairs of the middle portion 42 without connectors 30 attached thereto.

In some embodiments, adjacent strut members 34 of each peak 22 and valley 24 of the fifth strut column 58 are angularly offset from one another. In some embodiments, strut members 34 are offset by angles $\theta'$, $\rho'$, $\phi'$, and $\omega'$, respectively. As shown in FIG. 4B, angles $\theta'$, $\rho'$, $\phi'$, and $\omega'$ are all the same. In some embodiments, $\theta'$, $\rho'$, $\phi'$, and $\omega'$ are 40 degrees when the stent 10 is in an expanded configuration. In some embodiments, the strut pair nodes 48 of the fifth and sixth strut columns 58, 60 are equally spaced along the length of the strut column. In some embodiments, the strut pair nodes 48 of the fourth, fifth, and sixth strut columns 56, 58, 60 are equally spaced along the length of the strut column. In some embodiments, for example where the strut pair nodes 48 of the fifth and sixth strut columns 58, 60 are equally spaced, the strut pair nodes 48 of the strut pairs of the middle portion 42 are not equally spaced along the length of the respective strut column 20. In some embodiments, angles $\theta'$, $\rho'$, $\phi'$, and $\omega'$ between adjacent struts 34 of the fifth strut column 58 are all the same and angles between adjacent struts 34 of the strut columns 20 of the middle portion 42 vary. For example, in some embodiments, strut pairs of the middle portion 42 having connectors 30 attached thereto have more acute, or closed, angles than strut pairs of the middle portion 42 without connectors 30 attached thereto.

In some embodiments, the stent comprises nitinol. In some embodiments, the stent can comprise NiTi having variable properties along the length or circumference of the stent. In this way, localized areas of the stent can be more or less strong than other areas of the stent. Localized areas of the stent can undergo focal heat treatments to achieve the desired design.

In some embodiments, the stent may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

In some embodiments, the stent comprises shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

In some embodiments, the stent is covered with a covering or membrane, for example ePTFE. The covering can also be placed on the inside of the stent, outside of the stent, in-between the open spaces of the stent structure, or combinations thereof.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

In some embodiments, the stent (or stents) can be used in a body lumen bifurcation, for example a vessel bifurcation.

In some embodiments, the stent can be used in an environment requiring a stent having flexibility, fatigue resistance, durability, and supplying requisite radial force. In some embodiments the stent is suited to be used in arteries of patient's leg. In some embodiments, the stent is configured for use in the iliac, superficial femoral artery (SFA) or infrapopliteal vessels. In some embodiments, the stent is highly conformable, resistant to kink and fracture, and yet maintains stent radial force. In some embodiments, the proximal end portion has greater flexibility than the middle portion. In some embodiments, the distal end portion has greater flexibility than the middle portion. Moreover, in some embodiments, the flexibility of the stent transitions smoothly along the length of the stent such that the proximal end portion is less flexible than the middle portion and the distal end portion is less flexible than the middle portion. In some embodiments, the middle portion has uniform bending, uniform axial displacement performance, and uniform durability throughout the length of the middle portion.

Description of some exemplary embodiments is contained in the following numbered paragraphs:

1. A stent comprising:
   a proximal end portion, a distal end portion, and a middle portion therebetween;
   the proximal end portion comprising a plurality of strut columns including first, second, and third strut columns;
   the distal end portion comprising a plurality of strut columns including fourth, fifth, and sixth strut columns;
   each of the first, second, third, fourth, fifth, and sixth strut columns comprising alternating peaks and valleys including at least four peaks and at least four valleys;
   each valley of the first strut column connected to one peak of the second strut column;
   one-half of the total number of valleys of the second strut column connected to peaks of the third strut column in a repeating pattern of connected and unconnected valleys, wherein the repeating pattern of connected and unconnected valleys comprises one connected valley followed by one unconnected valleys;
   one-quarter of the total number of peaks of the third strut column connected to the middle portion in a repeating pattern of connected and unconnected peaks, wherein the repeating pattern of connected and unconnected peaks comprises one peak connected to the middle portion followed by three peaks which are unconnected to the middle portion, the connected peaks connected to the middle portion via connecting struts;
   one-quarter of the total number of peaks of the fourth strut column connected to the middle portion in a repeating pattern of connected and unconnected peaks, wherein the repeating pattern of connected and unconnected peaks comprises one peak connected to the middle portion followed by three peaks which are unconnected to the middle portion, the connected peaks connected to the middle portion via connecting struts;
   one-half of the total number of peaks of the fifth strut column connected to valleys of the fourth strut column in a repeating pattern of connected and unconnected peaks, wherein the repeating pattern of connected and unconnected peaks comprises one connected peak followed by a second connected peak, the second connected peak followed by two unconnected peaks;
   each peak of the sixth strut column connected to one valley of the fifth strut column.

2. The stent of paragraph 1, wherein middle portion comprises a plurality of strut columns connected one to another by a plurality of connecting struts.

3. The stent of paragraph 2, wherein each of the strut columns of the middle portion comprises alternating peaks and valleys, the connecting struts connected to the peaks of the strut columns.

4. The stent of paragraph 3, wherein the peaks of each strut column of the middle portion are arranged in a repeating pattern of connected and unconnected peaks, half of the total number of peaks of each strut column of the middle portion comprising connected peaks.

5. The stent of paragraph 4, wherein half of the connected peaks of each strut column of the middle portion are connected to an immediately proximal strut column and half of the connected peaks of each strut column of the middle portion are connected to an immediately distal strut column.

6. The stent of paragraph 2, wherein the connected peaks of the third strut column connected to the valleys of the second strut column are circumferentially offset from the connected peaks of the third strut column connected to the middle portion.

7. The stent of paragraph 6, wherein the connected peaks of the fourth strut column connected to the middle portion are circumferentially offset from the connected valleys of the fourth strut column.

8. The stent of paragraph 7, wherein each connecting strut connecting the peaks of the fourth strut column to the middle portion circumferentially bisects the two unconnected peaks of the repeating pattern of the fifth strut column.

9. The stent of paragraph 1 further comprising a plurality of radiopaque marker housings connected to the peaks of the first strut column and the valleys of the sixth strut column.

10. The stent of paragraph 9, wherein each radiopaque marker housing comprises an annular disc.

11. A stent comprising:
   a proximal end portion, a distal end portion, and a middle portion therebetween;
   the proximal end portion comprising a plurality of strut columns including first, second, and third strut columns;
   the distal end portion comprising a plurality of strut columns including fourth, fifth, and sixth strut columns;
   each of the first, second, third, fourth, fifth, and sixth strut columns comprising alternating peaks and valleys including at least four peaks and at least four valleys;
   valleys of the second strut column connected to peaks of the third strut column in a repeating pattern of connected and unconnected valleys;
   valleys of the fourth strut column connected to peaks of the fifth strut column in a repeating pattern of connected and unconnected valleys, wherein the repeating pattern of the connected and unconnected valleys of the second strut column is different from the repeating pattern of the connected and unconnected valleys of the fourth strut column.

12. A stent comprising:
   a proximal end portion, a distal end portion, and a middle portion therebetween;
   the proximal end portion comprising serpentine bands, the serpentine bands of the proximal end portion consisting of three interconnected serpentine bands including a first proximal serpentine band, a second intermediate serpentine band, and a third distal serpentine band,
   the distal end portion comprising serpentine bands, the serpentine bands of the distal end portion consisting of three interconnected serpentine bands including a fourth proximal serpentine band, a fifth intermediate serpentine band, and a sixth distal serpentine band,
   each of the first proximal serpentine band, the second intermediate serpentine band, and the third distal serpentine band comprising a plurality of peaks and valleys, each valley of the first proximal serpentine band connected to a peak of the second intermediate serpentine band, half of the valleys of the second intermediate serpentine band connected to peaks of the third distal serpentine band in a proximal repeating pattern;
   each of the fourth proximal serpentine band, the fifth intermediate serpentine band, and the sixth distal serpentine band comprising a plurality of peaks and valleys, each peak of the sixth distal serpentine band connected to a valley of the fifth intermediate serpentine band, half of the peaks of the fifth intermediate serpentine band connected to valleys of the fourth proximal serpentine band in a distal repeating pattern;
   the proximal repeating pattern being different than the distal repeating pattern.

13. The stent of paragraph 12, wherein the proximal repeating pattern consists of every other valley of the second intermediate serpentine band being connected to a peak of the third distal serpentine band.

14. The stent of paragraph 13, wherein the distal repeating pattern consists of two adjacent peaks of the fifth intermediate serpentine band being connected to valleys of the fourth proximal serpentine band followed by two adjacent peaks of the fifth intermediate serpentine band being unconnected to valleys of the fourth proximal serpentine band.

15. The stent of paragraph 14, wherein the middle portion comprises a plurality of serpentine bands.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A stent comprising:
   a proximal end portion, a distal end portion, and a middle portion therebetween;
   the proximal end portion comprising a plurality of strut columns including first, second, and third strut columns;
   the distal end portion comprising a plurality of strut columns including fourth, fifth, and sixth strut columns;
   each of the first, second, third, fourth, fifth, and sixth strut columns comprising alternating peaks and valleys including at least four peaks and at least four valleys;
   each valley of the first strut column connected to one peak of the second strut column;
   one-half of the total number of valleys of the second strut column connected to peaks of the third strut column in a repeating pattern of connected and unconnected valleys, wherein the repeating pattern of connected and unconnected valleys comprises one connected valley followed by one unconnected valley;
   one-quarter of the total number of peaks of the third strut column connected to the middle portion in a repeating pattern of connected and unconnected peaks, wherein the repeating pattern of connected and unconnected peaks comprises one peak connected to the middle portion followed by three peaks which are unconnected to the middle portion, the connected peaks connected to the middle portion via connecting struts;

one-quarter of the total number of peaks of the fourth strut column connected to the middle portion in a repeating pattern of connected and unconnected peaks, wherein the repeating pattern of connected and unconnected peaks comprises one peak connected to the middle portion followed by three peaks which are unconnected to the middle portion, the connected peaks connected to the middle portion via connecting struts;

one-half of the total number of peaks of the fifth strut column connected to valleys of the fourth strut column in a repeating pattern of connected and unconnected peaks, wherein the repeating pattern of connected and unconnected peaks comprises one connected peak followed by a second connected peak, the second connected peak followed by two unconnected peaks;

each peak of the sixth strut column connected to one valley of the fifth strut column;

wherein the strut columns are connected to one another via connecting struts, the connecting struts connecting the first strut column to the second strut column and the fifth strut column to the sixth strut column having a first length, the connecting struts connecting the second strut column to the third strut column and the fourth strut column to the fifth strut column having a second length, the first length being shorter than the second length.

2. The stent of claim 1, wherein middle portion comprises a plurality of strut columns connected one to another by a plurality of connecting struts.

3. The stent of claim 2, wherein each of the strut columns of the middle portion comprises alternating peaks and valleys, the connecting struts connected to the peaks of the strut columns.

4. The stent of claim 3, wherein the peaks of each strut column of the middle portion are arranged in a repeating pattern of connected and unconnected peaks, half of the total number of peaks of each strut column of the middle portion comprising connected peaks.

5. The stent of claim 4, wherein half of the connected peaks of each strut column of the middle portion are connected to an immediately proximal strut column and half of the connected peaks of each strut column of the middle portion are connected to an immediately distal strut column.

6. The stent of claim 2, wherein the connected peaks of the third strut column connected to the valleys of the second strut column are circumferentially offset from the connected peaks of the third strut column connected to the middle portion.

7. The stent of claim 6, wherein the connected peaks of the fourth strut column connected to the middle portion are circumferentially offset from the connected valleys of the fourth strut column.

8. The stent of claim 7, wherein each connecting strut connecting the peaks of the fourth strut column to the middle portion circumferentially bisects the two unconnected peaks of the repeating pattern of the fifth strut column.

9. The stent of claim 1 further comprising a plurality of radiopaque marker housings connected to the peaks of the first strut column and the valleys of the sixth strut column.

10. The stent of claim 9, wherein each radiopaque marker housing comprises an annular disc.

11. A stent comprising:
a proximal end portion, a distal end portion, and a middle portion therebetween;
the proximal end portion comprising a plurality of strut columns including first, second, and third strut columns;
the distal end portion comprising a plurality of strut columns including fourth, fifth, and sixth strut columns;
each of the first, second, third, fourth, fifth, and sixth strut columns comprising alternating peaks and valleys including at least four peaks and at least four valleys;
valleys of the second strut column connected to peaks of the third strut column in a repeating pattern of connected and unconnected valleys;
valleys of the fourth strut column connected to peaks of the fifth strut column in a repeating pattern of connected and unconnected valleys, wherein the repeating pattern of the connected and unconnected valleys of the second strut column is different from the repeating pattern of the connected and unconnected valleys of the fourth strut column; and
wherein the strut columns are connected to one another via connecting struts, the connecting struts connecting the first strut column to the second strut column and the fifth strut column to the sixth strut column having a first length, the connecting struts connecting the second strut column to the third strut column and the fourth strut column to the fifth strut column having a second length, the first length being shorter than the second length.

12. A stent comprising:
a proximal end portion, a distal end portion, and a middle portion therebetween;
the proximal end portion comprising serpentine bands, the serpentine bands of the proximal end portion consisting of three interconnected serpentine bands including a first proximal serpentine band, a second intermediate serpentine band, and a third distal serpentine band,
the distal end portion comprising serpentine bands, the serpentine bands of the distal end portion consisting of three interconnected serpentine bands including a fourth proximal serpentine band, a fifth intermediate serpentine band, and a sixth distal serpentine band,
each of the first proximal serpentine band, the second intermediate serpentine band, and the third distal serpentine band comprising a plurality of peaks and valleys, each valley of the first proximal serpentine band connected to a peak of the second intermediate serpentine band, half of the valleys of the second intermediate serpentine band connected to peaks of the third distal serpentine band in a proximal repeating pattern;
each of the fourth proximal serpentine band, the fifth intermediate serpentine band, and the sixth distal serpentine band comprising a plurality of peaks and valleys, each peak of the sixth distal serpentine band connected to a valley of the fifth intermediate serpentine band, half of the peaks of the fifth intermediate serpentine band connected to valleys of the fourth proximal serpentine band in a distal repeating pattern;
the proximal repeating pattern being different than the distal repeating pattern;
wherein adjacent serpentine bands are connected to one another via connecting struts, the connecting struts connecting the first serpentine band to the second serpentine band and the fifth serpentine band to the sixth serpentine band having a first length, the connecting struts connecting the second serpentine band to the third serpentine band and the fourth serpentine band to the fifth serpentine band having a second length, the second length being longer than the first length.

13. The stent of claim 12, wherein the proximal repeating pattern consists of every other valley of the second intermediate serpentine band being connected to a peak of the third distal serpentine band.

14. The stent of claim 13, wherein the distal repeating pattern consists of two adjacent peaks of the fifth intermediate serpentine band being connected to valleys of the fourth proximal serpentine band followed by two adjacent peaks of the fifth intermediate serpentine band being unconnected to valleys of the fourth proximal serpentine band.

15. The stent of claim 14, wherein the middle portion comprises a plurality of serpentine bands.

* * * * *